US00PP10289P

United States Patent [19]

Krans et al.

[11] Patent Number: Plant 10,289

[45] Date of Patent: Mar. 17, 1998

[54] 'MS-EXPRESS' BERMUDAGRASS

[75] Inventors: Jeffrey V. Krans; H. Wayne Philley, both of Mississippi State, Miss.

[73] Assignee: Mississippi State University, Mississippi State, Miss.

[21] Appl. No.: 582,963

[22] Filed: Jan. 4, 1996

[51] Int. Cl.[6] ..... A01H 5/00

[52] U.S. Cl. ..... Plt./90

[58] Field of Search ..... Plt./90

[56] References Cited

PUBLICATIONS

Krans, V.J. et al., "Registration of 'MS–Express' Bermudagrass" Crop Science 35:1507.

*Primary Examiner*—James R. Feyrer

*Attorney, Agent, or Firm*—Oblon, Spivak, McClelland, Maier, & Neustadt, P.C.

[57] ABSTRACT

An improved Bermudagrass plant, having superior properties, suitable for a variety of turf applications, is disclosed. The Bermudagrass is characterized by a medium green color, high-head density, moderate seed-head density, fine-leaf texture, good fall color retention, average sod strength, excellent cold tolerance, good shade tolerance as compared to other Bermudagrasses, good dollar spot, and good leaf-spot resistance.

1 Drawing Sheet

BACKGROUND OF THE NEW PLANT

The present invention relates to a new and distinct variety of Bermudagrass, which has excellent turfgrass quality, good pest resistance and above-average environmental stress hardiness. The inventive Bermudagrass is suitable for use on residential lawns, sports fields, golf fairways and tess.

The inventive Bermudagrass is characterized by a medium green color, high-shoot density, moderate seed head-density, fine-leaf texture, good fall color retention, average sod strength, excellent cold tolerance, good shade tolerance as compared to other Bermuda grasses, good dollar spot and good leaf-spot resistance.

BRIEF DESCRIPTION OF THE FIGURES

The plant is illustrated in FIGS. 1–6, which are color photographs of the inventive Bermudagrass.

Figure 1:
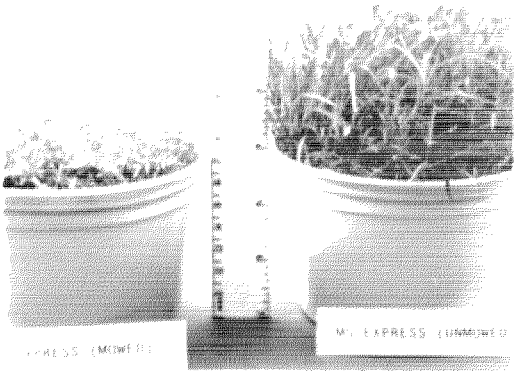
FIG. 1 reflects whole plant features of mowed and unmowed turf.

MS-Express (experimental name MSB 20) is a distinct genotype of Cynodon that was developed and is vegatatively propagated at the Plant Science Research Center, Mississippi Agricultural and Forestry Experiment Station, Mississippi State, Miss. MS-Express originated from a single clone collected, from the 10th fairway at the Shady Oaks Country Club, Jackson, Miss. on Aug. 21, 1980. Persons knowledgeable of Shady Oaks Country Club's history said that this fairway was established with Bermudagrass seed in the 1913, has existed as a golf fairway since its original planting, and had not been intentionally replanted with Bermudagrass seed, sprigs, plugs or sod since 1913.

MS-Express's origin may be from anyone of the following sources: (a) a seed within the original seed lot; (b) a seed or plant introduced unintentionally to this site; or (c) a plant which developed as a result of an environmentally selected mutations.

The identifying features of the original clone of MS-Express were a medium green color, very fine leaf texture, prostrate leaf growth, and a high shoot density. The size of the original clone was approximately 2 ft in diameter. A 4 inch diameter plug was removed from the center of the clone and transplanted to a Bermudagrass nursery located at the Plant Science Research Center. MS-Express was 1 to 72 ecotypes of Bermudagrass planted and maintained in this nursery.

MS-Express was evaluated for 5 years in this nursery. During this period, MS-Express maintained its original green color, very fine leaf texture, prostrate growth of leaves, and high shoot density.

In 1986, MS-Express was included in a regional Bermudagrass evaluation trial located at 15 sites encompassing 11 states. Data was collected from 1986 to 1990. The findings from this study confirmed MS-Express's light to medium green color, prostrate leaf growth, and high shoot density.

Morphological Description

MS-Express has a medium leaf width (1.6 to 2.0 mm), short leaf length (17.8 to 29.8 mm), medium internode length (8.1 to 14.1 mm), medium internode diameter, (0.78 to 1.12 mm), and medium node diameter (1.03 to 1.47 mm) (Table 1).

Seed Head Density

The seed head density of MS-Express was measured at 3 location for 2 or 3 years depending on location (Table 2). At all three locations, MS-Express had slightly higher than average seed head density compared to the other Bermudagrasses tested.

Genetic Color

The genetic color of MS-Express was visually rated at 7 locations for 1 or 2 years depending on location (Table 3). At all locations, MS-Express's color was rated light to medium green. The stolons are light green and rhizomes are white.

The color designation of MS-Express is 7.5 GY 5/8 using a Munsell color chart rating.

Shoot Density

The shoot density of MS-Express was measured at 2 location for 1 or 2 years depending on location (Table 4). MS-Express has a high shoot density that ranked average or slightly higher compared to the other Bermudagrasses tested.

Shade Tolerance

The shade tolerance of MS-Express was measured at 1 location for 2 years (Table 5). MS-Express has a good tolerance to shade that ranked above average compared to the other Bermudagrasses tested.

Ploidy Level and Chromosome Number

MS-Express's ploidy level and chromosome number were determined and compared to other Bermudagrasses (Table 6). MS-Express was found to be a triploid with 27 chromosomes.

Turfgrass Quality Rating

The overall turf quality of MS-Express was measured at 15 locations for 1, 2, or 3 years depending on location (Table 7). MS-Express has excellent turfgrass quality. In comparison to other Bermudagrasses tested, MS-Expressed at or near the top of the rankings depending on location.

Leaf Texture

Leaf texture based on a visual comparison was measured at 8 locations for 1 or 2 years depending on location (Table 8). MS-Express has a fine leaf texture that ranked well above average when compared to the other Bermudagrasses tested.

Establishment Rate

The establishment rate of MS-Express was measured at 6 locations during the 1986 establishment year (Table 9). MS-Express had the highest establishment rate 4 to 5 weeks after planting compared to the other Bermudagrasses tested.

Fall Color Retention

Fall color retention of MS-Express was measured during the month of November at 6 locations for 1 or 3 years depending on location (Table 10). MS-Express had good fall color retention that ranked at or slightly less than average when compared to other the other Bermudagrasses tested.

Unmowed Height and Sod Strength

The unmowed height and sod strength of MS-Express was measured at 1 location for 1 year and 1 location for 2 years, respectively (Table 11). MS-Express had a low unmowed height and average sod strength compared to the other Bermudagrasses tested.

Low Temperature Kill

The low temperature kill of MS-Express was measured at 1 location for 2 consecutive years (Table 12). During both years, MS-Express showed better than average low temperature tolerance compared to the other Bermudagrasses tested.

Disease Resistance

MS-Express's resistance to leafspot (Helminthosporium spp.) and dollar spot (Sclerotinia spp.) was measured at 1 location for 2 years (Table 13). MS-Express showed good resistance to leafspot and slightly above average susceptibility to dollar spot compared to other Bermudagrasses tested.

Distinguishing Features of MS-Express

Figure 2:
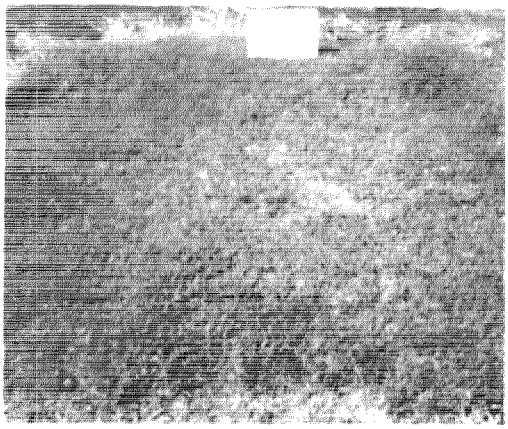
FIG. 2 is a photograph of a field plot of mowed turf.
Figure 3:
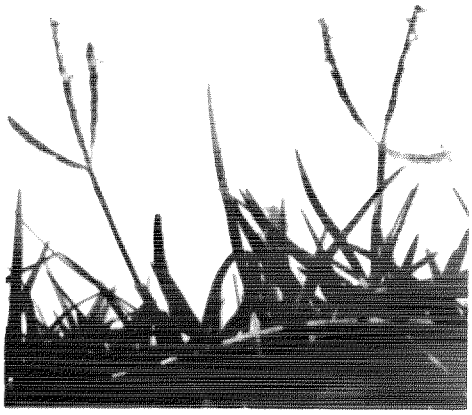
FIG. 3 is a photograph of a typical inflorescence structure showing three racemes per stalk.
Figure 4:
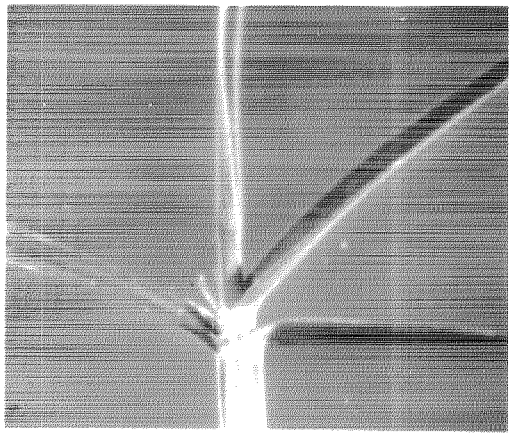
FIG. 4 is a photograph reflecting the leaf blade and sheath features of the inventive plant.
Figure 5:
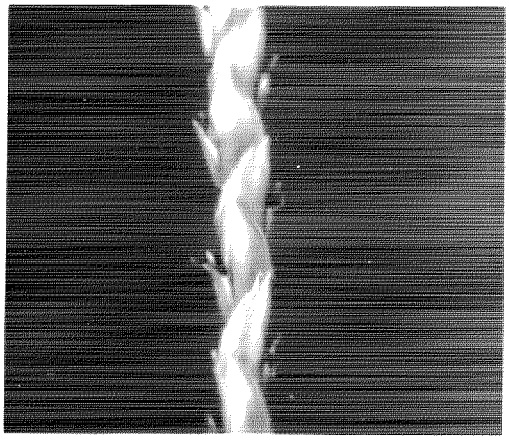
FIG. 5 is a photograph reflecting an abaxial view of spikelets of the inventive Bermudagrass.
Figure 6:
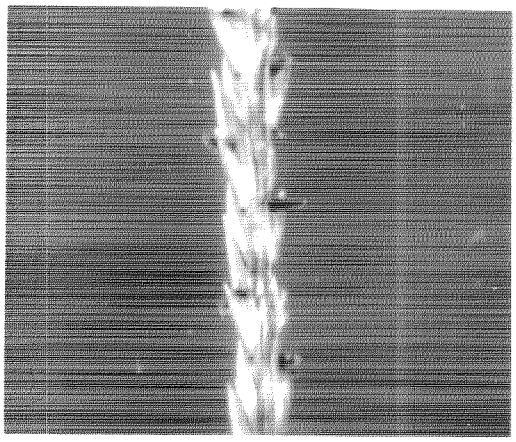
FIG. 6 is a photograph reflecting an adaxial view of spikelets of the inventive Bermudagrass.

MS-Express can be distinguished by morphological and turf performance characteristics. MS-Express has high turf density and quality as illustrated in pot and field plot culture (FIG. 1 and 2). MS-Express's shoot structure is pilose on the abaxial and adaxial leaf blade surfaces, pubescence tufted at the ligule margins, and glabrous on the adaxial leaf surface and sheath (FIG. 4). MS-Express has a raceme inflorescence structure with 3 racemes attached per stalk in a single whorl (FIG. 3). Spikelet density is one spikelet attached every 1.73 mm on the raceme stalk. Length of an average spikelet is 2.30 mm with glumes extending ⅓ to ½ the length of a floret (FIG. 5 and 6). The flower of MS-Express has a purple stigma and yellow anthers.

MS-Express has a narrower leaf than MS-Choice and Midiron, but a wider leaf width than MS-Pride, Tifgreen, Tifway II, and Tifway (Table 1). Leaf length of MS-Express is shorter than Midiron and Tufcote. There were no difference in internode length between MS-Express and the other Bermudagrasses tested. The internode and node diameters of MS-Express were larger than MS-Pride, Tifway II, and Tifway, but smaller than MS-Choice and Texturf 10. Seed head density of MS-Express was higher than MS-Choice, Tifway, Tifway II, Texturf 10, Tufcote, Midiron, and MS-Pride (Table 2).

MS-Express has turf performance characteristics that distinguish it from other Bermudagrasses. Compared to other fine textured Bermudgrasses, MS-Express has a significantly faster rate of establishment (Table 9). This feature is important under putting green management because rapid establishment reflects a shortened time prior to playability. In addition, MS-Express showed excellent tolerance to winter kill (Table 12) and a fine leaf texture (Table 8). These characteristics are important because Bermudagrass winter kill is common in the South and fine texture is necessary for putting green quality.

MS-Express, like all turf grasses, has a tendency to thatch. The tendency to thatch in this grass is limited. The thatch is comprised of dead leaves, dead or living stolons and dead or living crowns. In contrast to other Bermudagrasses, MS-Express has an average tendency to thatch.

The mowing height range for MS-Express is from 3/16–¾ inches. This Bermudagrass is suitable for use for golf putting greens.

Other performance characteristics of MS-Express ranked above average and included good turf quality, high shoot density, good fall color retention, good shade tolerance, and good disease resistance.

The following additional distinctive features are noted:

(a) Leaf color is lime green and rated a 7.5 GY 5/8 based on a Munsell® color chart for plant tissue. There is no anthocyanin pigmentation expressed in leaves during the fall. The average leaf width is 1.8 mm and average length 23.8 mm.

(b) The grass has a dense canopy of leaves erect from a prostrate base of creeping, strong stolons. Rhizomes are branched profusely. Stolon color is 5 GY 6/8 based on a Munsell® color chart for plant tissue. There is no anthocyanin pigmentation expressed in stolons during the fall. The average stolon internode diameter is 0.95 mm, the average stolon node diameter is 1.25 mm, and average stolon internode length is 11.1 mm.

(c) The grass has an extensive fibrous root system initiated from the nodes of stolons and rhizomes.

(d) Leaves are folded in the bud shoot; the blades are mostly flat or slightly V-shaped with only the midvein visible; and the leaf tip is tapered to an acute apex.

(e) The grass has a moderate frequency of inflorescence formation having an average density of 235 inflorescences per square meter. Average height of culms is 30 mm. The inflorescences consists of 2 to 3 digitate spikes at the top of the main stem, folded down at a 30 to 40 degree angle from vertical, spikelets sessiled and closely appressed. The average length of each spike is 32 mm.

(f) The grass blade is pilose on the abaxial and adaxial surface. The ligule consists of a fringe of hairs. The sheath is glabrous, split with margins overlapping, and pubescence tufted at the side of the ligule. The collar is a continuous narrow band, glabrous and auricles are absent.

(g) The spikelets are glabrous in two rows, blunt at their base and pointed at their tips. Spikelets are attached an average distance of 1.73 mm along the spikes, borne singly on short branches. The length of an average spikelet is 2.3 mm with glumes extending ⅓ to ½ the length of a floret. The spikelet has stigmas of light purple-red color rated as a 5 RP 7/8 based on a Munsel® color chart for plant tissue.

(h) The grass has a somatic chromosome number of 27 and classed as a triploid.

TABLE 1

A quantitative comparison of morphological features for describing the whole plant morphology of MS-Express and eight other bermudagrasses.

| Bermudagrass Entry | Leaf Width | Leaf Length | Internode Length mm | Internode Diameter | Node Diameter |
|---|---|---|---|---|---|
| MS-Pride | 1.3 | 29.0 | 11.8 | 0.65 | 0.85 |
| MS-Choice | 2.4 | 22.6 | 10.2 | 1.43 | 1.65 |
| Midiron | 2.3 | 35.8 | 15.7 | 1.00 | 1.35 |
| Texturf 10 | 1.8 | 22.9 | 9.4 | 1.28 | 1.28 |
| Turfcote | 1.7 | 33.7 | 12.9 | 1.10 | 1.33 |
| MS-Express | 1.8 | 23.8 | 11.1 | 0.95 | 1.25 |
| Tifgreen | 1.3 | 22.3 | 9.4 | 0.90 | 1.22 |
| TIfway II | 1.3 | 27.2 | 10.9 | 0.64 | 0.85 |
| Tifway | 1.2 | 28.2 | 11.8 | 0.67 | 0.89 |
| LSD (.05) | 0.22 | 5.66 | 3.02 | 0.172 | 0.222 |
| Mean | 1.65 | 27.27 | 11.47 | 0.93 | 1.18 |

TABLE 2

Comparative seed head density of MS-Express and nine other bermudagrasses.

| Bermudagrass Entry | Field Plot Locations | | |
|---|---|---|---|
| | Starkville Mississippi | Las Cruces New Mexico | Blacksburg Virginia |
| MS-Choice | 8.8[1] | 9.0 | 9.0 |
| Tifgreen | 4.0 | 4.7 | 6.2 |
| Tifway | 7.0 | 7.8 | 8.2 |
| Tifway II | 7.3 | 7.8 | 7.8 |
| Texturf 10 | 5.3 | 8.0 | 6.7 |

TABLE 2-continued

Comparative seed head density of MS-Express and nine other bermudagrasses.

| Bermudagrass Entry | Field Plot Locations | | |
|---|---|---|---|
| | Starkville Mississippi | Las Cruces New Mexico | Blacksburg Virginia |
| Tufcote | 7.5 | 5.3 | 7.7 |
| Midiron | 5.7 | 5.0 | 7.3 |
| MS-Pride | 7.3 | 7.9 | 7.7 |
| MS-Express | 4.3 | 5.1 | 6.5 |
| Arizona Common | 4.7 | 5.9 | 6.7 |
| LSD (.05) | 0.77 | 0.67 | 0.82 |
| Mean | 6.2 | 6.6 | 7.4 |
| Cultivar X Year interaction. | * | ** | ** |
| Years data was collected. | 1987<br>1988 | 1986<br>1987<br>1988 | 1987<br>1988 |

[1]Seed head density rating based on a 1 to 9 scale; with 1 = high seed head density and 9 = no seed heads.
*,** Significant at the .05 and .01 level of probability, respectively.

TABLE 3

Comparative genetic color of MS-Express and nine other bermudagrasses.

| Bermudagrass Entry | Field Plot Location | | | |
|---|---|---|---|---|
| | Tucson Arizona | Santa Ana California | Gainsville Florida | Starkville Mississippi |
| MS-Choice | 7.0[1] | 9.0 | 7.3 | 7.7 |
| Tifgreen | 6.3 | 7.0 | 5.2 | 5.0 |
| Tifway | 6.7 | 8.0 | 7.0 | 6.3 |
| Tifway II | 6.3 | 8.0 | 6.8 | 7.0 |
| Texturf 10 | 6.3 | 7.7 | 5.8 | 5.3 |
| Tufcote | 6.7 | 6.7 | 5.8 | 5.0 |
| Midiron | 6.7 | 7.7 | 5.7 | 5.3 |
| MS-Pride | 6.0 | 7.7 | 6.8 | 7.0 |
| MS-Express | 6.3 | 7.7 | 6.2 | 5.0 |
| Arizona Common | 5.3 | 5.7 | 5.2 | 5.0 |
| LSD (.05) | NS | 0.75 | 0.55 | 0.65 |
| Mean | 6.4 | 7.5 | 6.2 | 5.9 |
| Cultivar X Year interaction. | | | ** | |
| Years data was collected. | 1987 | 1987 | 1987<br>1988 | 1988 |

| Bermudagrass Entry | Field Plot Location | | |
|---|---|---|---|
| | Las Cruces New Mexico | Stilwater Oklahoma | Cleveland Texas |
| MS-Choice | 7.5 | 8.0 | 8.7 |
| Tifgreen | 6.8 | 6.3 | 7.7 |
| Tifway | 7.0 | 7.7 | 9.0 |
| Tifway II | 7.7 | 6.0 | 8.0 |
| Texturf 10 | 7.0 | 7.3 | 8.0 |
| Tufcote | 7.2 | 4.7 | 7.3 |
| Midiron | 6.3 | 6.7 | 7.0 |
| MS-Pride | 7.7 | 7.0 | 8.7 |
| MS-Express | 6.7 | 6.3 | 7.7 |
| Arizona Common | 5.5 | 6.0 | 6.7 |
| LSD (.05) | NS | 1.08 | 0.80 |
| Mean | 6.9 | 6.6 | 7.9 |
| Cultivar X Year interaction. | NS | | |
| Years data was collected. | 1986<br>1987 | 1988 | 1988 |

[1]Genetic color rating based on a 1 to 9 scale; with 1 = light green color and 9 = dark green color.
*,** Significant at the .05 and .01 level of probability, respectively.

TABLE 4

Comparative shoot density of MS-Express and nine other bermudagrasses.

| Bermudagrass Entry | Field Plot Location: Las Cruces New Mexico | Stillwater Oklahoma |
|---|---|---|
| MS-Choice | 8.4[1] | 8.0 |
| Tifgreen | 8.4 | 7.7 |
| MS-Pride | 8.1 | 7.3 |
| Texturf 10 | 7.8 | 8.0 |
| Tifway | 7.7 | 7.7 |
| Midiron | 7.9 | 7.0 |
| Tifway II | 7.3 | 7.7 |
| MS-Express | 7.3 | 7.3 |
| Tufcote | 6.3 | 7.7 |
| Arizona Common | 3.9 | 6.0 |
| LSD (0.05) | 0.61 | 0.95 |
| Mean | 7.3 | 7.5 |
| Entry x Year Interaction | ** | NA |
| Year(s) data was recorded | 1986 1987 | 1987 |

[1]Shoot density rating based on a visual scale; with 1 = low density and 9 = high density.
*, ** Significant at the 0.05 and 0.01 level of probability, respectively.

TABLE 5

Comparative shade tolerance of MS-Express and nine other bermudagrasses[1].

| Bermudagrass Entry | Shade Tolerance |
|---|---|
| MS-Choice | 4.9[2] |
| MS-Pride | 4.5 |
| Tifgreen | 4.3 |
| MS-Express | 4.3 |
| Tifway II | 3.8 |
| Tifway | 3.7 |
| Texturf 10 | 3.5 |
| Tufcote | 3.4 |
| Arizona Common | 2.5 |
| Midiron | 2.1 |
| LSD (0.05) | 0.39 |
| Mean | 3.7 |
| Cultivar X Year interaction | ** |
| Years data was collected | 1987 1988 |

[1]Field plots located in Starkville, MS.
[2]Shade tolerance based on a visual scale of 1 to 9: with 9 = excellent shade tolerance and 1 = poor shade tolerance.
*, ** Significant at the 0.05 and 0.01 level of probability, respectively.

TABLE 6

The ploidy level and chromosome number of MS-Express and nine other bermudagrasses.

| Bermudagrass Entry | Ploidy Level | Chromosome Number |
|---|---|---|
| MS-Choice | Tetraploid | 36[1] |
| Texturf 10 | | 36 |
| Turfcote | | 36 |
| Midiron | | 36 |
| Arizona Common | | 36 |
| MS-Express | Triploid | 27 |
| MS-Pride | | 27 |

TABLE 6-continued

The ploidy level and chromosome number of MS-Express and nine other bermudagrasses.

| Bermudagrass Entry | Ploidy Level | Chromosome Number |
|---|---|---|
| Tifgreen | | 27 |
| Tifway | | 27 |
| Tifway II | | 27 |

[1]Chromosome numbers were determined using squashes of root tips.

TABLE 7

Comparative turfgrass quality of MS-Express and nine other bermudagrasses.

| Bermudagrass Entry | Field Plot Location: Tucson Arizona | Santa Ana California | Riverside California | Gainsville Florida |
|---|---|---|---|---|
| MS-Choice | 7.5[1] | 6.3 | 4.9 | 5.7 |
| Tifgreen | 7.3 | 5.8 | 5.4 | 4.8 |
| Tifway | 7.8 | 6.5 | 5.5 | 5.8 |
| Tifway II | 7.9 | 6.5 | 5.7 | 5.7 |
| Texturf 10 | 7.8 | 5.8 | 5.1 | 5.1 |
| Tufcote | 7.3 | 5.4 | 5.2 | 5.6 |
| Midiron | 6.2 | 5.8 | 4.9 | 4.9 |
| MS-Pride | 8.3 | 6.5 | 5.3 | 6.0 |
| MS-Express | 7.8 | 5.9 | 5.8 | 5.2 |
| Arizona Common | 5.5 | 4.4 | 4.7 | 4.9 |
| LSD (.05) | 0.54 | 0.33 | 0.55 | 0.32 |
| Mean | 7.3 | 5.9 | 5.2 | 5.4 |
| Cultivar X Year interaction. | | ** | NS | ** |
| Year(s) data was collected. | 1988 | 1986 1987 | 1986 1987 1988 | 1987 1988 1988 |

| Bermudagrass Entry | Field Plot Location: Manhattan Kansas | Wichita Kansas | Baton Rogue Louisiana | Silver Springs Maryland |
|---|---|---|---|---|
| MS-Choice | 6.9 | 8.0 | 7.0 | 6.0 |
| Tifgreen | 6.9 | 7.8 | 7.7 | 6.2 |
| Tifway | 6.3 | 8.2 | 7.6 | 6.3 |
| Tifway II | 6.5 | 8.4 | 7.6 | 6.4 |
| Texturf 10 | 6.7 | 7.9 | 6.9 | 5.3 |
| Tufcote | 6.9 | 7.7 | 7.3 | 5.8 |
| Midiron | 6.7 | 7.7 | 6.7 | 5.4 |
| MS-Pride | 6.5 | 8.3 | 7.5 | 6.4 |
| MS-Express | 6.8 | 8.1 | 7.6 | 7.7 |
| Arizona Common | 5.0 | 5.9 | 6.3 | 5.0 |
| LSD (.05) | 0.38 | 0.30 | 0.59 | NS |
| Mean | 6.5 | 7.8 | 7.2 | 6.1 |
| Cultivar X Year interaction. | ** | ** | * | |
| Year(s) data was collected. | 1987 1988 | 1986 1987 | 1987 1988 1988 | 1988 |

| Bermudagrass Entry | Field Plot Location: Starkville Mississippi | Las Cruces New Mexico | Cleveland Texas | Beltsville Maryland |
|---|---|---|---|---|
| MS-Choice | 6.1[1] | 7.3 | 8.0 | 7.0 |
| Tifgreen | 7.4 | 6.3 | 9.0 | 7.3 |
| Tifway | 6.7 | 7.0 | 7.7 | 6.6 |
| Tifway II | 6.9 | 7.5 | 8.0 | 6.8 |
| Texturf 10 | 5.6 | 6.8 | 5.7 | 6.5 |
| Tufcote | 5.5 | 6.2 | 5.7 | 6.7 |
| Midiron | 5.1 | 6.5 | 5.3 | 5.8 |
| MS-Pride | 6.9 | 7.2 | 8.0 | 6.9 |
| MS-Express | 7.6 | 6.7 | 8.7 | 7.0 |

TABLE 7-continued

Comparative turfgrass quality of MS-Express and nine other bermudagrasses.

| | | | | |
|---|---|---|---|---|
| Arizona Common | 4.1 | 3.8 | 4.0 | 4.5 |
| LSD (.05) | 0.19 | 0.49 | 1.14 | 0.38 |
| Mean | 6.2 | 6.5 | 7.0 | 6.5 |
| Cultivar X Year interaction. | ** | ** | NA | ** |
| Year(s) data was collected. | 1986<br>1987<br>1988 | 1986<br>1987<br>1988 | 1988 | 1986<br>1987<br>1988 |

| Bermudagrass Entry | Field Plot Location<br>Blacksburg Virginia | Blackstone Virginia | Virginia Beach Virginia |
|---|---|---|---|
| MS-Choice | 5.9 | 6.8 | 6.7 |
| Tifgreen | 5.9 | 6.8 | 6.2 |
| Tifway | 6.5 | 7.0 | 6.3 |
| Tifway II | 6.1 | 6.8 | 6.9 |
| Texturf 10 | 6.0 | 6.6 | 5.7 |
| Tufcote | 5.8 | 6.4 | 4.9 |
| Midiron | 5.0 | 5.8 | 5.9 |
| MS-Pride | 5.8 | 6.8 | 6.4 |
| MS-Express | 6.5 | 6.8 | 6.0 |
| Arizona Common | 4.2 | 5.0 | 3.9 |
| LSD (.05) | 0.43 | 0.38 | 0.77 |
| Mean | 5.8 | 6.5 | 5.9 |
| Cultivar X Year interaction. | * | ** | NA |
| Year(s) data was collected. | 1986<br>1987<br>1988 | 1986<br>1988 | 1986 |

[1]Turfgrass quality ratings based on a 1 to 9 scale with 1 = poor turfgrass quality and 9 = excellent turf quality.
*, ** Significant at the .05 and .01 level of probability, respectively.

TABLE 8

Comparative leaf texture of MS-Express and nine other bermudagrasses.

| Cultivar | Field Plot Locations<br>Tucson Arizona | Wichita Kansas | Gainsville Florida | Starkville Mississippi |
|---|---|---|---|---|
| MS-Choice | 5.3[1] | 6.7 | 5.7 | 5.0 |
| Tifgreen | 7.3 | 9.0 | 7.5 | 7.7 |
| Tifway | 7.0 | 7.7 | 7.8 | 6.0 |
| Tifway II | 6.3 | 8.3 | 8.2 | 6.0 |
| Texturf 10 | 5.7 | 8.0 | 5.5 | 5.0 |
| Tufcote | 5.7 | 6.0 | 7.0 | 5.0 |
| Midiron | 5.3 | 4.0 | 5.8 | 5.0 |
| MS-Pride | 6.7 | 7.3 | 8.0 | 6.0 |
| MS-Express | 7.7 | 9.0 | 7.3 | 8.0 |
| Arizona Common | 4.3 | 3.7 | 2.7 | 4.3 |
| LSD (.05) | 0.92 | 0.68 | 1.01 | 0.43 |
| Mean | 6.1 | 7.0 | 6.6 | 5.8 |
| Cultivar X Year interaction. | | | ** | |
| Year(s) data was collected. | 1987 | 1986 | 1987<br>1988 | 1988 |

| Cultivar | Field Plot Locations<br>Las Cruces New Mexico | Baton Rogue Louisiana | Virginia Virginia |
|---|---|---|---|
| MS-Choice | 6.5 | 6.3 | 4.7 |
| Tifgreen | 9.0 | 9.0 | 7.0 |
| Tifway | 8.2 | 9.0 | 6.0 |
| Tifway II | 8.3 | 9.0 | 5.7 |
| Texturf 10 | 5.8 | 6.3 | 5.7 |
| Tufcote | 6.7 | 9.0 | 3.7 |

TABLE 8-continued

Comparative leaf texture of MS-Express and nine other bermudagrasses.

| | | | |
|---|---|---|---|
| Midiron | 6.8 | 7.7 | 4.3 |
| MS-Pride | 8.5 | 9.0 | 6.0 |
| MS-Express | 8.8 | 9.0 | 6.0 |
| Arizona Common | 4.2 | 6.3 | 2.3 |
| LSD (.05) | 0.79 | 0.79 | 1.19 |
| Mean | 7.3 | 8.1 | 5.1 |
| Cultivar X Year interaction. | ** | | |
| Year(s) data was collected. | 1986<br>1987 | 1988 | 1988 |

[1]Leaf texture rating based on a 1 to 9 scale; with 1 = coarse leaf texture and 9 = fine leaf texture.
*, ** Significant at the 0.05 and 0.01 level of probability, respectively.

TABLE 9

Comparative establishment rate 4–5 weeks after planting of MS-Express and 27 other bermudagrasses.[1]

| Bermudagrass Entry | Field Plot Locations<br>Starkville Mississippi | Beltsville Maryland | Blacksburg Virginia |
|---|---|---|---|
| MS-Express | 3.0 | 7.0 | 2.7 |
| Az-Common | 6.3 | 7.0 | 2.7 |
| Numex Sahara | 5.7 | 7.3 | 2.3 |
| NMS 15 | 4.7 | 8.0 | 3.3 |
| FB-119 | 4.3 | 5.7 | 2.7 |
| NMS 2 | 4.0 | 8.0 | 2.7 |
| Tifgreen | 3.3 | 6.0 | 2.3 |
| RS-1 | 3.3 | 6.0 | 3.0 |
| A-29 | 3.3 | 6.7 | 1.7 |
| Midlawn | 3.3 | 5.0 | 3.0 |
| Vamont | 3.7 | 5.7 | 2.3 |
| NM 43 | 2.7 | 5.7 | 2.0 |
| Sonesta | 2.7 | 6.3 | 2.7 |
| MS-Choice | 3.3 | 4.3 | 2.3 |
| NMS 4 | 3.7 | 5.7 | 2.0 |
| Texturf 10 | 3.0 | 4.7 | 2.0 |
| Midfield | 4.3 | 6.0 | 2.3 |
| Guymon | 3.7 | 5.3 | 2.7 |
| NM 471 | 3.3 | 4.0 | 2.0 |
| NM 507 | 3.3 | 4.0 | 2.0 |
| Tifway | 2.3 | 4.0 | 2.3 |
| Midiron | 3.3 | 4.7 | 1.7 |
| Tufcote | 3.0 | 4.0 | 2.0 |
| Tifway II | 2.3 | 4.3 | 2.0 |
| NM 72 | 2.7 | 2.7 | 2.0 |
| MS-Pride | 1.7 | 3.0 | 1.7 |
| NM 375 | 2.7 | 2.3 | 1.7 |
| CT-23 | 2.0 | 3.0 | 1.7 |
| LSD (.05) | 1.3 | 1.1 | 0.7 |

| Bermudagrass Entry | Field Plot Locations<br>Blackstone Virginia | Virginia Beach Virginia | Mean |
|---|---|---|---|
| MS-Express | 7.3 | 5.3 | 5.1 |
| Az-Common | 7.3 | 5.3 | 5.0 |
| Numex Sahara | 4.7 | 3.3 | 4.7 |
| NMS 15 | 4.0 | 3.3 | 4.7 |
| FB-119 | 6.3 | 4.0 | 4.6 |
| NMS 2 | 4.3 | 3.7 | 4.5 |
| Tifgreen | 5.3 | 4.7 | 4.3 |
| RS-1 | 4.3 | 3.7 | 4.1 |
| A-29 | 4.7 | 4.0 | 4.1 |
| Midlawn | 4.3 | 3.7 | 3.9 |
| Vamont | 4.3 | 4.3 | 3.9 |
| NM 43 | 4.3 | 3.3 | 3.8 |
| Sonesta | 3.7 | 3.7 | 3.9 |
| MS-Choice | 4.7 | 3.7 | 3.7 |

TABLE 9-continued

Comparative establishment rate 4–5 weeks after planting of MS-Express and 27 other bermudagrasses.[1]

| | | | |
|---|---|---|---|
| NMS 4 | 3.7 | 2.7 | 3.5 |
| Texturf 10 | 4.0 | 4.0 | 3.5 |
| Midfield | 2.7 | 2.0 | 3.5 |
| Guymon | 3.0 | 2.7 | 3.5 |
| NM 471 | 4.3 | 3.0 | 3.3 |
| NM 507 | 4.7 | 2.3 | 3.3 |
| Tifway | 4.7 | 2.0 | 3.1 |
| Midiron | 3.0 | 2.3 | 3.0 |
| Tufcote | 3.3 | 1.3 | 2.7 |
| Tifway II | 2.7 | 2.0 | 2.7 |
| NM 72 | 3.3 | 1.7 | 2.5 |
| MS-Pride | 3.7 | 2.0 | 2.4 |
| NM 375 | 2.3 | 2.0 | 2.2 |
| CT-23 | 1.7 | 1.0 | 1.9 |
| LSD (.05) | 1.5 | 1.3 | 0.5 |

[1]Comparative establishment rate based on a visual scale of 1 to 9; with 1 = minimal cover and 9 = complete cover.

TABLE 10

Comparative fall color retention of MS-Pride and nine other bermudagrasses.

| Bermuda-grass Entry | Field Plot Location | | | | |
|---|---|---|---|---|---|
| | Beltsville Maryland | Raleigh North Carolina | Starkville Mississ-ippi | Las Cruces New Mexico | Loc. 2 New Mexico |
| MS-Pride | 5.3[1] | 6.7 | 6.5 | 4.3 | 5.3 |
| Tifway | 4.8 | 6.7 | 6.2 | 4.6 | 5.7 |
| Tifway II | 4.5 | 7.3 | 6.5 | 4.4 | 5.7 |
| Tufcote | 2.8 | 6.3 | 5.3 | 3.2 | 3.3 |
| Midirion | 2.3 | 3.7 | 4.2 | 3.1 | 3.3 |
| Texturf 10 | 2.2 | 5.3 | 3.2 | 2.6 | 5.0 |
| MS-Choice | 2.0 | 5.7 | 4.2 | 3.4 | 4.3 |
| Tifgreen | 2.0 | 6.3 | 3.2 | 2.0 | 4.0 |
| MS-Express | 1.7 | 6.7 | 3.0 | 2.1 | 4.3 |
| Arizona Common | 1.7 | 5.7 | 4.5 | 3.4 | 2.3 |
| LSD (0.05) | 0.68 | 1.54 | 0.43 | 0.76 | 1.74 |
| Mean | 2.9 | 6.0 | 4.7 | 3.3 | 4.3 |
| Cultivar x Year interaction | ** | NA | ** | ** | NA |
| Year(s) data was collected | 1986 1987 | 1986 | 1986 1988 | 1986 1987 1988 | 1988 |

[1]Color ratings based on a visual scale of color with; 9 = green color and 1 = brown color.
*, ** Significant at the 0.05 and 0.01 level of probability, respectively.

TABLE 11

Comparative height of unmowed plots and sod strength of MS-Express and nine other bermudagrasses.

| Bermudagrass Entry | Plant Measurement | |
|---|---|---|
| | Unmoved Height cm | Sod Strength lbs |
| Arizona Common | 31.7[1] | 26.8[2] |
| Tufcote | 8.7 | 39.3 |
| Midiron | 5.7 | 39.5 |
| Tifway II | 5.0 | 121.5 |
| MS-Choice | 4.3 | 65.5 |

TABLE 11-continued

Comparative height of unmowed plots and sod strength of MS-Express and nine other bermudagrasses.

| Bermudagrass Entry | Plant Measurement | |
|---|---|---|
| | Unmoved Height cm | Sod Strength lbs |
| Texturf 10 | 4.3 | 77.8 |
| Tifway | 4.3 | 95.2 |
| MS-Express | 4.0 | 86.7 |
| MS-Pride | 4.0 | 157.7 |
| Tifgreen | 3.3 | 74.7 |
| LSD (0.05) | 1.8 | 34.5 |
| Mean | 7.5 | 78.5 |
| Entry x Year Interaction | NA | NS |
| Year(s) data was collected | 1986 | 1987 1988 |
| Location | Las Cruces New Mexico | Starkville Mississippi |

[1]The shoot height was determined by measuring the height of the grass at its maximum length above the soil surface.
[2]Sod strength was determined by measuring the amount of force (lbs) required to shear an 18 × 24 × 1" section of sod.

TABLE 12

Comparative turf mortality due to winter kill of MS-Express and nine other bermudagrasses[1].

| Bermudagrass Entry | Year | |
|---|---|---|
| | 1987 | 1988 |
| | % turf mortality | |
| Tufcote | 0[2] | 0 |
| Tifgreen | 3.3 | 1.7 |
| MS-Express | 1.7 | 5.0 |
| Texturf 10 | 3.3 | 10.0 |
| MS-Pride | 5.0 | 25.0 |
| Midiron | 11.7 | 11.7 |
| Tifway | 5.0 | 36.7 |
| Tifway II | 5.0 | 36.7 |
| MS-Choice | 11.7 | 36.7 |
| Arizona Common | 35.0 | 88.3 |
| LSD (0.05) | 11.6 | 12.9 |
| Mean | 8.2 | 25.2 |

[1]Field plot were located in Beltsville, MD.
[2]The % of plot area lost to low temperature killed was based on a visual evaluation of turf lost immediately following spring green-up in May.

TABLE 13

Comparative leafspot (Helminthosporium spp.) and dollarspot (Sclerotinia spp.) disease resistance of MS-Express and nine other bermudagrasses.

| Bermudagrass Entry | Disease Rating | |
|---|---|---|
| | Helminthosporium | Dollar Spot |
| MS-Pride | 8.8[1] | 8.4 |
| MS-Express | 8.7 | 7.7 |
| Tifgreen | 8.3 | 7.3 |
| Tifway II | 8.3 | 8.5 |
| Texturf 10 | 8.2 | 8.7 |
| Tifway | 8.2 | 8.7 |
| MS-Choice | 7.9 | 6.4 |
| Midiron | 7.8 | 8.7 |
| Tufcote | 7.0 | 8.8 |
| Arizona Common | 6.2 | 8.6 |

TABLE 13-continued

Comparative leafspot (Helminthosporium spp.) and dollarspot (Sclerotinia spp.) disease resistance of MS-Express and nine other bermudagrasses.

| Bermudagrass | Disease Rating | |
|---|---|---|
| Entry | Helminthosporium | Dollar Spot |
| LSD (0.05) | 0.73 | 0.83 |
| Mean | 7.9 | 8.2 |
| Entry x Year Interaction | ** | ** |
| Year(s) data was collected | 1986<br>1988 | 1986<br>1988 |

TABLE 13-continued

Comparative leafspot (Helminthosporium spp.) and dollarspot (Sclerotinia spp.) disease resistance of MS-Express and nine other bermudagrasses.

| Bermudagrass | Disease Rating | |
|---|---|---|
| Entry | Helminthosporium | Dollar Spot |

[1]Disease rating based on a visual scale of 1 to 9; with 9 = no disease damage (excellent disease resistance) and 1 = high incidence of disease damage (poor disease resistance).
*, ** Significant at the 0.05 and 0.01 level of probability, respectively.

What is claimed is:

1. A Bermudagrass plant substantially as described and illustrated in the specification herein.

* * * * *